US012605074B1

(12) United States Patent
    Tucker

(10) Patent No.: US 12,605,074 B1
(45) Date of Patent: Apr. 21, 2026

(54) APPARATUS FOR PROVIDING INDICES OF ELASTICITY OR STIFFNESS OF AN ARTERY

(71) Applicant: Trevor Tucker, Ottawa (CA)

(72) Inventor: Trevor Tucker, Ottawa (CA)

( * ) Notice: Subject to any disclaimer, the term of this patent is extended or adjusted under 35 U.S.C. 154(b) by 0 days.

(21) Appl. No.: 19/222,376

(22) Filed: May 29, 2025

Related U.S. Application Data

(63) Continuation-in-part of application No. 19/034,962, filed on Jan. 23, 2025, now abandoned.

(51) Int. Cl.
    *A61B 5/02* (2006.01)
    *A61B 5/00* (2006.01)
(52) U.S. Cl.
    CPC ........ *A61B 5/02007* (2013.01); *A61B 5/7235* (2013.01); *A61B 5/7278* (2013.01)
(58) Field of Classification Search
    None
    See application file for complete search history.

(56) References Cited

U.S. PATENT DOCUMENTS 6,647,287 B1 11/2003 Peel, III
2012/0123240 A1* 5/2012 Silber ................ A61B 5/02007
                                                            600/410

OTHER PUBLICATIONS

Calabia et al. Doppler ultrasound in the measurement of pulse wave velocity: agreement with the Complior method; Cardiovascular Ultrasound 2011, 9:13 (Year: 2011).*

* cited by examiner

*Primary Examiner* — Jay B Shah
(74) *Attorney, Agent, or Firm* — Teitelbaum & Bouevitch; Neil Teitelbaum

(57) ABSTRACT

An apparatus for measuring stiffness of a blood vessel such as an artery acquires a flow velocity waveform which is used to determine Natural Resonant Frequency and Pulse Wave Velocity for an arterial location. Pulse Wave Velocity is an established index of arterial stiffness while Natural Resonant Frequency is an index of arterial stiffness. The apparatus includes a flow velocity waveform detecting unit, a flow velocity and timing data extraction unit, and natural resonant frequency and pulse wave velocity determination units.

9 Claims, 9 Drawing Sheets

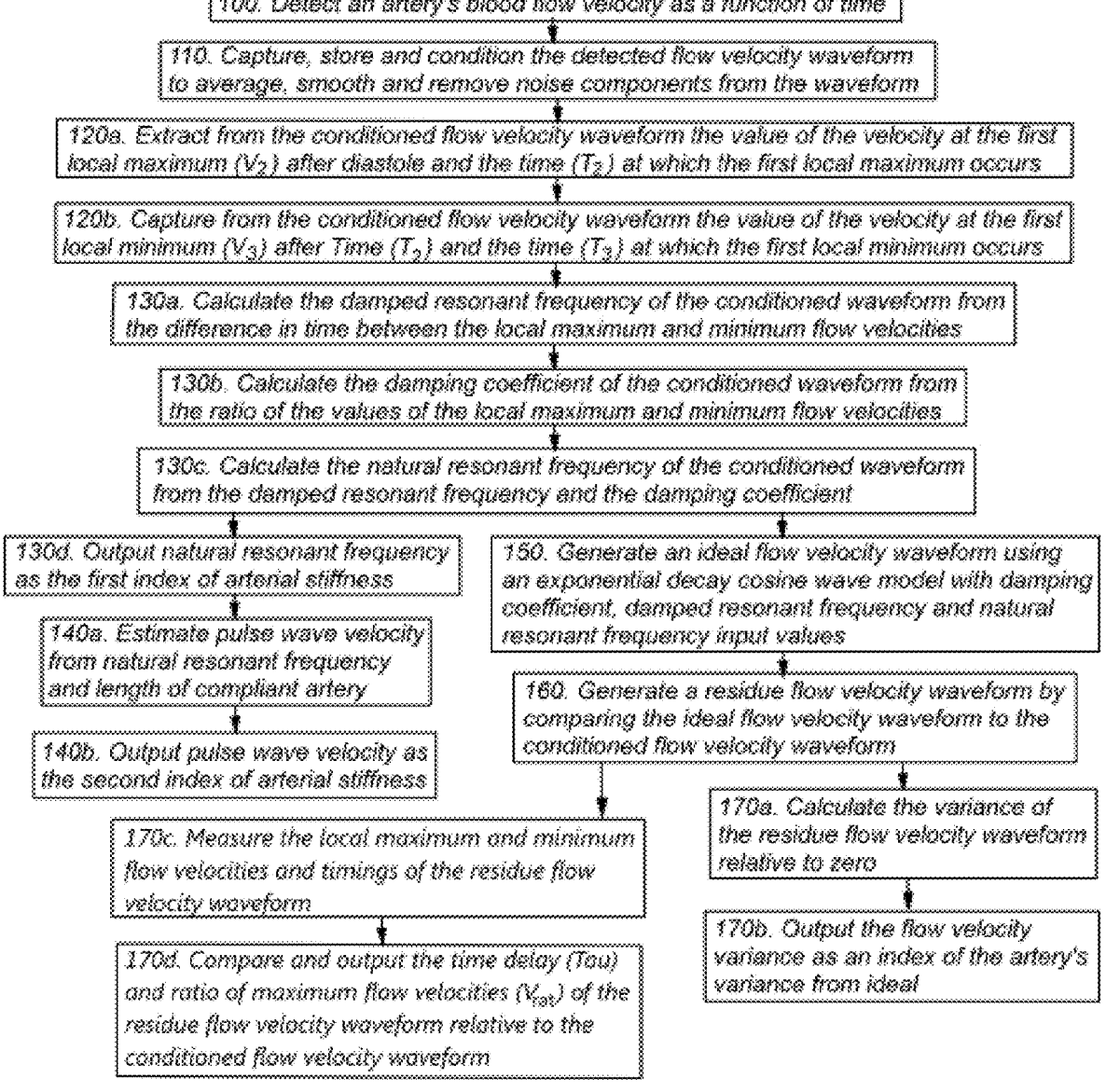

100. Detect an artery's blood flow velocity as a function of time

110. Capture, store and condition the detected flow velocity waveform to average, smooth and remove noise components from the waveform 120a. Extract from the conditioned flow velocity waveform the value of the velocity at the first local maximum ($V_2$) after diastole and the time ($T_2$) at which the first local maximum occurs 120b. Capture from the conditioned flow velocity waveform the value of the velocity at the first local minimum ($V_3$) after Time ($T_2$) and the time ($T_3$) at which the first local minimum occurs 130a. Calculate the damped resonant frequency of the conditioned waveform from the difference in time between the local maximum and minimum flow velocities 130b. Calculate the damping coefficient of the conditioned waveform from the ratio of the values of the local maximum and minimum flow velocities 130c. Calculate the natural resonant frequency of the conditioned waveform from the damped resonant frequency and the damping coefficient 130d. Output natural resonant frequency as the first index of arterial stiffness 150. Generate an ideal flow velocity waveform using an exponential decay cosine wave model with damping coefficient, damped resonant frequency and natural resonant frequency input values 140a. Estimate pulse wave velocity from natural resonant frequency and length of compliant artery 160. Generate a residue flow velocity waveform by comparing the ideal flow velocity waveform to the conditioned flow velocity waveform 140b. Output pulse wave velocity as the second index of arterial stiffness 170a. Calculate the variance of the residue flow velocity waveform relative to zero 170c. Measure the local maximum and minimum flow velocities and timings of the residue flow velocity waveform 170b. Output the flow velocity variance as an index of the artery's variance from ideal 170d. Compare and output the time delay (Tou) and ratio of maximum flow velocities ($V_{2t}$) of the residue flow velocity waveform relative to the conditioned flow velocity waveform

Figure 6

APPARATUS FOR PROVIDING INDICES OF ELASTICITY OR STIFFNESS OF AN ARTERY

CROSS-REFERENCE TO RELATED APPLICATIONS

The present invention is a Continuation in part from U.S. patent application Ser. No. 19/034,962 filed Jan. 23, 2025, which is incorporated herein by reference.

BACKGROUND

Arteries normally stiffen with patients' aging over many decades, stiffening that is most often associated with the onset of arteriosclerosis and the development of atherosclerotic plaques. Abnormally elevated arterial stiffness, particularly for blood flow in the central arteries, is widely associated, in the medical community, with increases in cardiovascular disease risk and all cause mortality.

The phase velocity of blood pressure pulses propagating in arteries, commonly referred to in the medical community as Pulse Wave Velocity (PWV), is widely accepted as a surrogate measure or index of arterial "stiffness".

A well-known non-invasive technique for the measurement of PWV uses two pulse pressure or arterial wall displacement sensors positioned on the skin surface over spatially separated arterial locations. The calculation of PWV is based on the measurement of the time difference for arrival of pressure pulses to propagate to each of the pressure or wall displacement sensors, which are of measurable separation distance and of measurable distance from the heart to each sensor. Normally, the sensors are placed over arterial locations where the artery is close to the surface where pulse pressure or arterial wall displacement is most easily measured.

Such a "dual pulse sensor" PWV measurement approach normally involves the propagation of pressure pulses through multiple individual arterial segments, each with differing stiffnesses and diameters. The dual pulse pressure and wall displacement sensor techniques do not measure PWV at one specific location on a specific artery but rather measure PWV as averaged over several arterial segments. In current medical practice, the measurement of an "average" PWV for pressure pulses to propagate through multiple arterial segments, using a dual-sensor technique, is the most common approach to the non-invasive assessment of arterial "stiffness".

The relationship between PWV and arterial elasticity is provided by the Moens-Korteweg equation, which is given by equation (1):

$$PWV = \sqrt{Eh/\rho d} \qquad (1)$$

Where "E" is the elastic modulus of the arterial wall, which is of thickness "h", and "$\rho$", the blood's density, and "d", the diameter of the artery, as shown in FIG. 1. The conditions for the physics validity of the Moens-Korteweg equation (1) include:

a. Artery interior diameter: d>6 millimeters
  b. Artery wall thickness: h<d
  c. Arteries are straight.
  d. Blood flow is laminar.
  e. Blood is an incompressible fluid.

f Pulse propagation is unidirectional without reflection, and
  g. Each of E, h, $\rho$ and d are constant over the length of the artery.

The central artery's macrocirculation region, wherein arterial diameter is greater than 6 millimeters (mm), is the only region for which the Moens-Korteweg equation is, from a physics perspective, believed to be reasonably valid. A primary assumption in the derivation of the Moens-Korteweg equation is that the viscous resistance to flow is negligible, a condition that is applicable only to arteries of diameter greater than about 6 mm. For arterial diameters in the mesocirculation (with arterial diameter between 1 mm and 6 mm) the PWV decreases with decreases in arterial diameter, deviating from the dependence of PWV on arterial diameter as indicated by the Moen-Korteweg equation.

Often in the medical community, however, PWV is used as a measure of "stiffness" of all arteries, irrespective of arterial diameter. The medical community does not differentiate between PWV for macrocirculation arteries (d>6 mm) and for mesocirculation arteries (6 mm>d>1 mm), as a measure of arterial stiffness.

Central artery, or "Aortic", PWV is described in the medical community, as the "gold standard" for non-invasively measuring arterial "stiffness", as an index of cardiovascular disease risk. Aortic PWV is most often determined through the placement of pulse pressure or arterial wall displacement sensors, one over each of the carotid and the femoral arteries, two spatially separate arteries of measurable separation distance, and the measurement of the time difference for pressure pulses to propagate to each of the two sensors. The resulting PWV measurement, commonly referred to as the cfPWK is therefore a result of pulses' propagation through, not only the aorta (typical diameter, 16 to 22 mm), but also the carotid (typical diameter, 4 to 6 mm), iliac (typical diameter, 11 to 14 mm) and femoral arteries (typical diameter, 6 to 9 mm). Hence, cfPWV is not a measure of stiffness of any specific artery, particularly the aorta, rather is representative of the time required for pressure pulses to propagate from the heart to the carotid and to the femoral artery through several arteries, each of different stiffness and diameter.

Recently, a new and potentially better "gold standard" measurement for assessing cardiovascular disease risk, the gradient in PWV between central and peripheral arteries, has been proposed. PWV gradient is calculated by dividing the PWV measured on central arteries divided by the PWV measured on peripheral arteries. For example, the PWV gradient may be calculated as the ratio of the carotid-to-femoral PWV to the femoral-to-dorsal-pedis PWV In the condition wherein the impedance to pulsatile flow in the peripheral arteries does not match that in the central arteries, then pulsatile reflection occurs at the impedance mismatch or gradient. With pulsatile reflection, retrograde and antegrade pulse pressures augment one another while retrograde and antegrade pulsatile flows cancel one another, with both conditions representing increased risk of adverse cardiovascular events.

PWV measurement techniques require specialized sensors and are applicable primarily to measurements taken between shallow arteries located close to the skin surface. PWV measurement techniques are time consuming and provide only non-localized, averaged "stiffness" measures of multiple cascaded arteries.

Despite the wide recognition of the medical importance of arterial stiffness as a predictor of all-cause mortality, because of the time required to measure PWV using specialized sensors, it is rarely measured in clinical practice. Arterial stiffness measurement is currently carried out primarily in research laboratories and pharmaceutical trials. However, considerable scientific effort has been applied to adapting PWV measurements techniques for use in clinical settings.

SUMMARY

In accordance with an aspect of the disclosure there is provided an artery elasticity and stiffness measuring apparatus for measuring stiffness or elasticity of an artery at a measurement location about an artery, comprising:

a flow velocity detecting unit adapted to detect a plurality of blood flow velocities at a location of the artery;

an automatic capture and condition unit having memory means coupled to receive flow velocity data from the plurality of blood flow velocities, said automatic capture and condition unit adapted to extract, store, and condition a flow velocity waveform utilizing the flow velocity data so as to provide a conditioned flow velocity waveform related to the plurality of flow wave velocities;

a data point extraction unit adapted to receive the conditioned flow velocity waveform and automatically capture from the conditioned waveform a local maximum velocity of pulse flow velocity $V_2$ at a time $T_2$, and a-local minimum velocity of flow velocity $V_3$ at a time $T_3$;

a flow velocity parameter compute unit adapted to receive information processed by the data point extraction unit for automatically calculating a damped resonant frequency (DRF), a damping coefficient (DC) and a natural resonant frequency (NRF), related to the flow velocity waveform, in dependence upon a difference in the time between $T_3$ and $T_2$ and an absolute value of the ratio of $V_3$ to $V_2$, wherein the NRF is a measure of artery elasticity at the location in the artery, wherein NRF is related to pulse wave velocity (PWV) at the location, and wherein pulse wave velocity is an index of arterial stiffness at the location of the artery.

In accordance with another aspect of the disclosure there is provided a method of determining an index of elasticity at a location in the vasculature comprising:

detecting a plurality of blood flow wave velocities within the vasculature;

storing in a memory device flow wave velocity data corresponding to the plurality of detected blood flow wave velocities and automatically smoothing the flow wave velocity data to yield a conditioned flow velocity waveform related to the detected flow wave velocities;

extracting from the conditioned flow velocity waveform a local maximum velocity of flow velocity $V_2$ at time $T_2$, and a local minimum velocity of flow velocity $V_3$ at time $T_3$; wherein $T_2$ and T3 are measured relative to the foot of the flow velocity waveform and $V_2$ and $V_3$ are measured relative to the steady state value of flow velocity of the flow velocity waveform.

automatically calculating a damped resonant frequency (DRF), a damping coefficient (DC) and a natural resonant frequency (NRF), related to the flow velocity waveform, in dependence upon a difference in the time between $T_3$ and $T_2$ and an absolute value of the ratio of $V_3$ to $V_2$, wherein the NRF is a measure of vasculature elasticity at the location, and wherein NRF is related to pulse wave velocity at the location, and wherein pulse wave velocity an index of vascular stiffness at the location.

BRIEF DESCRIPTION OF THE DRAWINGS

Exemplary embodiments of the disclosure will be described in accordance with the drawings in which:

FIG. 6 is a flow diagram outlining the primary elements of this disclosure and the functional sequence executed by the primary components shown in FIG. 5.

DETAILED DESCRIPTION

It is the objective of this disclosure to provide a method and apparatus for measuring indices of arterial elasticity and stiffness within the time and equipment constraints imposed by typical medical (clinical) examination settings. The method and apparatus of this disclosure is based on an application of the engineering transmission line model of an elastic artery's response to an impulse of blood flow into the artery. The method and apparatus involve the measurement of the velocity of the blood's flow, as a function of time, as the elastic artery recovers from the initial impulse of input flow, after the left ventricle valve closes.

This disclosure provides a new method for measuring indices of vascular/arterial elasticity and stiffness, wherein the method is implementable, in widely used, existing blood flow velocity measurement apparatus such as pulse Doppler ultrasound, phase contrast magnetic resonance imaging and X-ray digital subtraction equipment, by personnel at the skill level of those who currently develop and modify such systems and apparatus.

The apparatus and method of this disclosure provide for a medically important, arterial health measurement diagnosis capability not currently offered by widely deployed and clinically used ultrasound, MRI and X-ray angiography systems.

The Moens-Korteweg (equation (1)), on which current PWV measurements techniques are based, indicates that the artery's elasticity, as quantified by the elastic modulus "E", is directly proportional to the square of the PWV (i.e. $E \propto PWV^2$).

Figure 1:
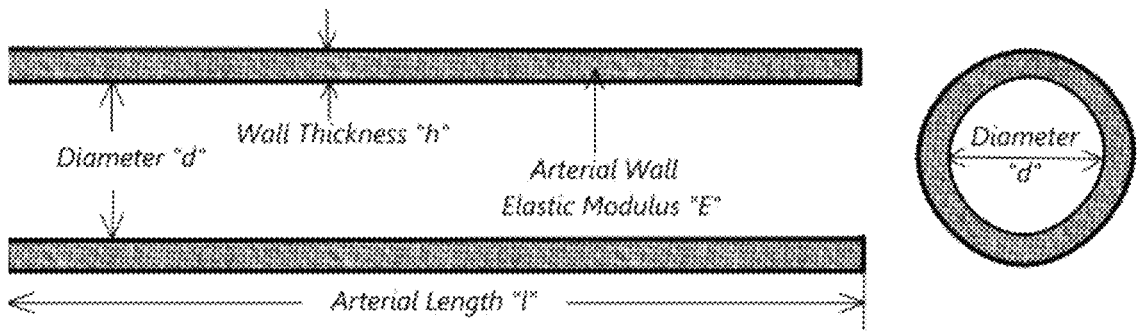
FIG. 1 is a diagrammatic representation of a length of an elastic vessel in which the primary parameters that characterize the stiffness of the vessel are identified.
Figure 2:
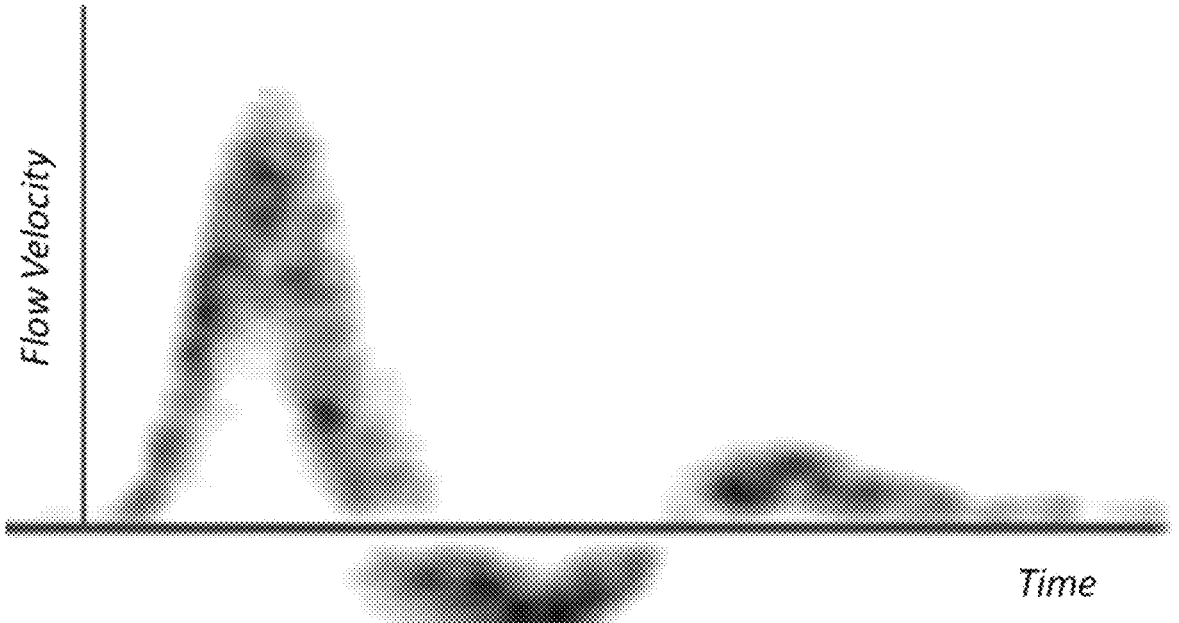
FIG. 2 is a prior art underdamped flow velocity waveform (FWV) measured in-vivo by Doppler ultrasound on a normal, healthy lower extremity artery, in a rested state.

In common usage "stiffness" and "elasticity" are related but distinct concepts. Stiffness normally refers to an object's resistance to deformation when an external force is applied, while elasticity normally refers to the recovery of the deformed object when an external deforming force is removed. This difference between stiffness and elasticity is demonstrated by the representative Doppler ultrasound flow velocity waveform (FVW) measured in an elastic central artery, as shown by the plot of FIG. 2. The rate of increase in flow velocity which occurs from the foot of the wave to the systolic maximum is a measure of the stiffness of the artery, while the rate of decrease after the systolic maximum, but before the foot of the next waveform, is a measure of the elasticity of the artery.

The flow velocity waveform, (FVW) is the velocity of blood flow as a function of time for the duration of a cardiac cycle, including both increasing and decreasing segments of flow velocity.

The flow velocity varies across the arterial luminal area at any instant in the cardiac cycle. The use of a measurement cell of finite size (or resolution) results in multiple velocities occurring simultaneously within the cell at any instant in the cardiac cycle. The spread in flow velocities at any instant in the measured waveform of one cardiac cycle results in the spread or width of the FVW plot as shown on the vertical (velocity) axis of the plot of FIG. 2. A measured FVW which consists of a spectrum of multiple simultaneous velocities is described here as an unconditioned FVW. An unconditioned FVW may also comprise the sum of multiple cardiac cycles of flow velocity waves, each synchronized and superimposed on, or added to, one another, instant-by-instant, for the duration of a cardiac cycle.

A FVW of the damped oscillatory form shown in FIG. 2, is described in medical practice as tri-phasic or multi-phasic, referring to the two or more "phases" of forward and reverse flow within a single cardiac cycle. An elastic artery's response waveform, after cessation of the input pulse, like that shown in FIG. 2, is that of a damped oscillating wave, implying a damping factor and a frequency of oscillation. In general, a FVW, while possessing a systolic forward flow velocity peak, may or may not include a phase of overshoot of the final steady state value of flow velocity, depending on the amount of damping associated with the artery's elasticity.

The representative FVW, as shown in FIG. 2, has the same basic attributes as a damped oscillating linear system. A second order differential equation, as provided in equation (2), offers the canonical form of a mathematical description of the response of a damped, oscillating, linear system, as a function of time, to an impulse of input flow.

$$\frac{d^2 V(t)}{dt^2} + 2\xi\omega_n \frac{dV(t)}{dt} + \omega_n^2 V(t) = 0 \tag{2}$$

The flow velocity time response characteristic, as determined by equation (2), is described by just two parameters, "$\xi$" the Damping Coefficient, also herein abbreviated as "DC", and "$\omega_n$", the Natural Resonant Frequency, also herein abbreviated "NRF". In principle, values for DC and NRF can be determined by taking two measurements of flow velocity at arbitrary points in time on a FVW and applying these measurements to an optimum curve fitting algorithm, which while analytically cumbersome, can derive values for DC and NRF.

This disclosure provides, not only for optimum curve fitting algorithms to measure arterial elasticity, but also for a simple algorithm, suitable for near real time execution, for application in clinical settings, by measuring flow velocity values at two local velocity maxima, specifically at peak systolic forward flow velocity and at peak overshoot flow velocity (in the reverse or negative flow direction in FIG. 2). FIG. 2 shows a representative underdamped FVW as measured by Doppler ultrasound for blood flow in a healthy macrocirculation artery. The representative FVW plot of FIG. 2 shows the existence and positions of maxima in local forward pulse flow velocity and local reverse overshoot pulse flow velocity.

The application of the engineering transmission line model to arterial pulse flow velocity, "V(t)", in an elastic artery, produces the second order differential equation (3):

$$\frac{d^2 V(t)}{dt^2} + \frac{R}{I}\frac{dV(t)}{dt} + \frac{1}{IC}V(t) = 0 \tag{3}$$

Where "R" is the resistance to pulsatile flow which is related to the blood's viscosity "$\mu$", the artery's length "L", and the artery's radius "r" by equation (4):

$$R \approx \frac{8\mu L}{\pi r^4} \tag{4}$$

And where "I" is the inertial reactance to pulsatile flow which is related to the density of the blood "$\rho$" and the artery's length and radius by equation (5):

$$I \approx \frac{\rho L}{\pi r^2} \tag{5}$$

And where "C" is the arterial wall's elastic reactance to pulsatile flow which is related to the thickness of the arterial wall "h", the elastic, or Young's modulus of elasticity of the arterial wall "E", and the artery's length and radius by equation (6):

$$C \approx \frac{2\pi L r^3}{Eh} \tag{6}$$

Combining and comparing the above equations (equations 2 to 6) provides the following parameter equivalences:

$$\omega_n^2 = \frac{1}{IC} \approx \frac{\pi r^2}{\rho L}\frac{Eh}{2\pi L r^3} = \frac{Eh}{\rho d L^2} \tag{7}$$

$$\xi\omega_n = \frac{R}{2I} \approx \frac{4\mu L}{\pi r^4}\frac{\pi r^2}{\rho L} = \frac{16v}{d^2} \tag{8}$$

Where "v" is the kinematic viscosity of the blood and is given by Equation (9):

$$v = \frac{\mu}{\rho} \tag{9}$$

Where a nominal value of "v" for whole blood at room temperature is $v \approx 3.8$ mm$^2$/sec.

Equation (7) shows that the Natural Resonant Frequency "$\omega_n$" is proportional to the square root of the product of the elastic modulus and the thickness of the arterial wall and is, therefore, a measure of arterial elasticity.

The objective of the apparatus and methodology of this disclosure, that of measuring indices of arterial elasticity and stiffness with sufficient simplicity and efficiency that they may be executed within medical clinical settings, is met by measuring Natural Resonant Frequency (NRF), Damped Resonant Frequency (DRF) and Damping Coefficient (DC), through the efficient and practical measurement of key velocities, and their timings, on clinically measured blood Flow Velocity Waveforms (FVWs).

Figure 3:
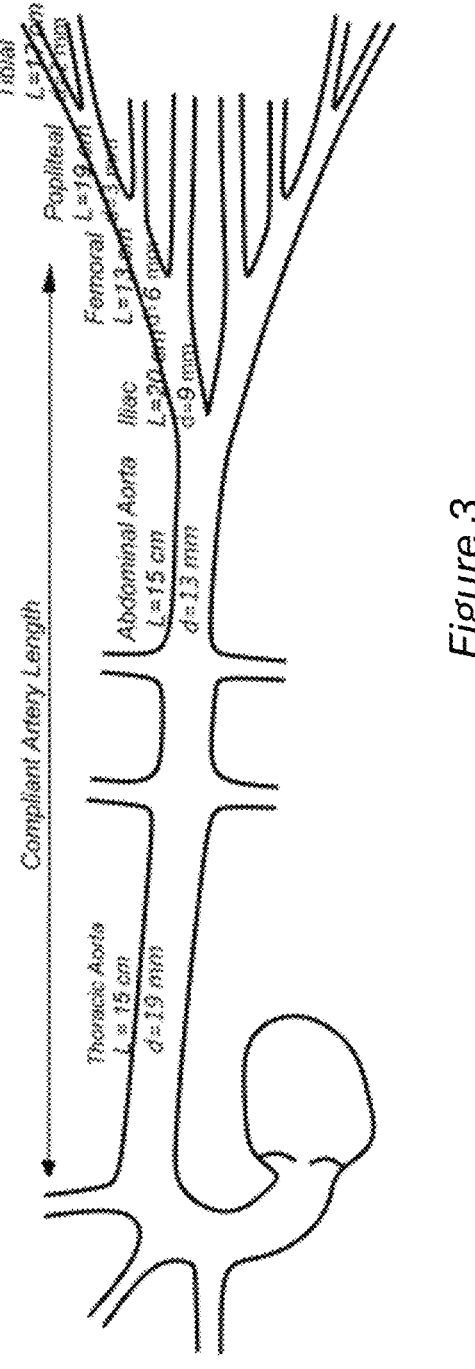
FIG. 3 is a diagrammatic representation of major central arteries, including typical values of arterial segment length and diameter.

Comparing equation (7) to the Moens-Korteweg equation, (i.e. to equation (1)) shows that the natural resonant frequency "$\omega_n$" is related to the pulse wave velocity (PWV) at the measurement location as given by Equation (10):

$$\omega_n \approx \frac{1}{L}\left(\frac{Eh}{d\rho}\right)^{\frac{1}{2}} = \frac{1}{L}PWV \tag{10}$$

Where "L" is the length of a primarily elastic central (macrocirculation) artery, wherein the diameter is greater than 6 mm, which is a sufficiently large diameter that the viscous resistive component of impedance to pulse flow is small compared to the elastic/inertial (reactive) component of impedance. The diameter of 6 mm corresponds to that of the distal femoral artery, representing the end of the negligible resistance portion (i.e. primarily elastic) of central arteries. As demonstrated in FIG. 3, the length of primarily elastic central arteries, from the aortic arch to the femoral artery, is comprised of a nominal length of 15 cm for the thoracic aorta, 15 cm for the abdominal aorta and 10 cm for the iliac artery length, totaling a length of primarily elastic artery of approximately 50 cm.

Referring to equation (10), the PWV has dependence on three variables, "E", "h" and "d", each of which may vary along the length of the elastic artery, implying that PWV also varies along the length of the artery.

For clarity, Equation (10) identifies a novel index of arterial elasticity, that of Natural Resonant Frequency "$\omega_n$" or "NRF", which is directly related to the long-established arterial stiffness index of pulse wave velocity (PWV), by the length of primarily elastic artery, wherein a primarily elastic artery is an artery in which the viscous resistance component of impedance is negligible compared to the elastic/inertial reactance component of impedance.

The critical arterial diameter, "$d_c$", at which the resistive component of impedance is equal to the reactive (elastic/inertial) component, is at the approximate center of the mesocirculation (arterial diameter greater than 1 mm, but less than 6 mm). Healthy macrocirculation arteries, whose diameter is greater than 6 mm, are primarily elastic and underdamped (i.e. possessing an overshoot response). In comparison, healthy microcirculation arteries, whose diameter is less than 1 mm, are primarily resistive and overdamped (i.e. possessing no overshoot response)

Applying the transmission line engineering model to arterial pulsatile flow produces an equation for the impedance "$Z_0$", to pulse flow per unit length of artery as given by Equation (11):

$$Z_0 = \left[\frac{I}{C}\right]^{0.5}\left[1 - \frac{jR}{\omega I}\right]^{0.5} \tag{11}$$

The "j" term in Equation (11) is an application of the engineering convention employed to describe the phase between the resistive and reactive (elastic/inertial) components of impedance. The resistive component of the artery's impedance is equal to the elastic/inertial (reactive) component, at the fundamental frequency of the heart rate (HR=$\omega$/$2\pi$), when the condition of Equation (12) is met:

$$R = \omega I = 2\pi I^* (HR) \tag{12}$$

Combining Equations (4), (5) and (12) results in an equation for the critical diameter "$d_c$", at which the resistive and reactive components of impedance per unit length are equal, as shown in Equation (13):

$$d_c = 4\left[\frac{v}{\pi * (HR)}\right]^{0.5} \tag{13}$$

Substituting values of v=3.8 mm$^2$/sec for the blood's kinematic viscosity and HR=1.2 beat/sec into Equation (13) results in a nominal value of $d_c \approx 4$ mm, which is near the center of the mesocirculation.

The solution to the canonical second order differential equation (2), in the case of the damping coefficient being less than unity, has an underdamped oscillating flow velocity solution of the form shown by equation (14):

$$V(t) = V_2\cos(\omega_d t)e^{-\xi\omega_n t} \tag{14}$$

Where $V_2$ is the maximum flow velocity, or systolic flow velocity, which occurs at the transition between the growth and decay phases of the FVW, (i.e. after the initial input pulse ceases upon closure of the left ventricle valve). The damping coefficient, "$\xi$", for the underdamped oscillating decay phase, has a value of less than one in healthy, elastic macrocirculation arteries, where "$\omega_n$" is the FVW's decay phase's Natural Resonant Frequency (NRF) and describes the frequency of oscillation under the condition that the value of damping coefficient is zero. The decay phase's natural resonant frequency, "$\omega_n$", is related to the decay phase's damped resonant frequency, "cod", and its damping coefficient, "a", by equation (15):

$$\omega_n = \omega_d/\sqrt{1 - \xi^2} \tag{15}$$

Figure 4:
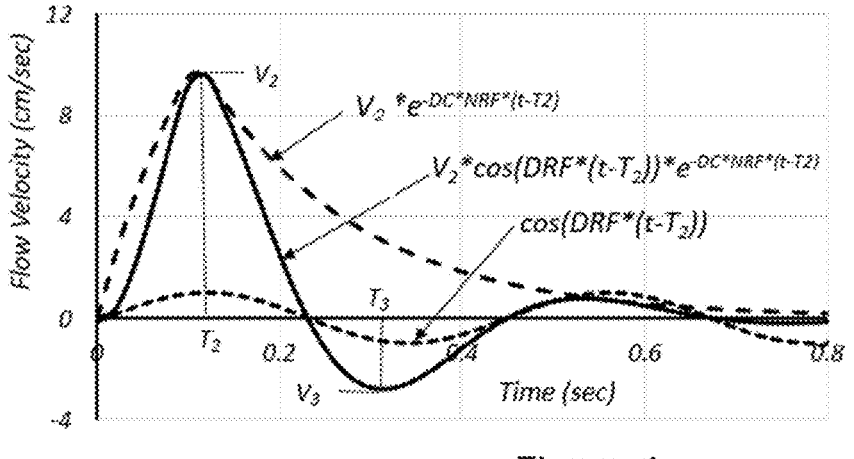
FIG. 4 is a diagrammatic representation of a computed flow velocity waveform showing the constituent components of cosine oscillation and exponential decay.

A calculated representative FVW, which is posited for healthy elastic macrocirculation arteries, as described by equation (14), for a single cardiac cycle, is as shown by the solid line in FIG. 4. Also shown in FIG. 4 are the cosine and exponential components, as shown in dashed lines which, together as described by equation (14), constitute a computed FVW.

Forward travelling FVWs may be partially reflected by abnormalities in arterial morphology, producing reverse travelling (antegrade) FVWs, which reduce, instant-by-instant, the magnitude of the forward traveling FVW The reverse travelling wave(s) will possess the same values of DC, DRF and NRF as the forward travelling FVW, except with a magnitude that is reduced by the magnitude of reflection at the abnormality and by the attenuation in the reflected wave's two-way travel to and from the reflecting site(s).

The ratio between the magnitude of the backward (antegrade) and forward FVWs at a measurement location is the Reflection Factor (RF) as defined by equation (16):

$$RF = \frac{V_B}{V_F} \tag{16}$$

Where "$V_F$" is the maximum systolic flow velocity for pulsatile flow in the forward direction (i.e. retrograde flow) and "$V_B$" is the maximum systolic flow velocity for pulsatile flow in the backward direction (i.e. antegrade flow).

The value of RF will be dependent on the distance from the morphology change(s) or abnormality(s) which reflect the impinging pulse wave, and the attenuation of the wave associated with the two-way transit of pulsatile wave(s) to and from the reflective site(s).

A general equation for the decay phase of a combined forward and single backward propagating flow velocity wave, reflected from a single site, is shown in equation (17):

$$V(t) = V_F e^{-\xi \omega_n t} \cos\left(\omega_n \sqrt{1-\xi^2}\, t\right) - V_B e^{-\xi \omega_n t} \cos\left(\omega_n \sqrt{1-\xi^2}\,(t+\tau)\right) \tag{17}$$

Where r is the time delay for the two-way transit of the reflected flow wave to and from the reflection site and includes any phase shift occurring on reflection from the reflecting morphology change.

If the reflected backward travelling wave is not negligible relative to the forward travelling wave, then more than two measurement points are required to determine the additional parameters of RF; the reflection factor, and r, the time delay between the forward travelling wave and the backward travelling wave. In this case, the parameters describing both forward and backward travelling waves are required and may be computed by applying established curve fitting algorithms and software operators to establish the best point-by-point match between equation (17) and a measured flow velocity waveform (FVW).

In arteries for which there is substantial sclerotic plaque development, or in arteries of the mesocirculation or microcirculation, arteries in which the viscous resistive impedance to pulse flow is comparable to or exceeds the elastic/inertial impedance to pulse flow, the elastic response to an impulse of input flow may be overdamped, with a damping coefficient that is greater than unity.

In the case of the damping coefficient being greater than unity, the solution to the canonical second order differential equation (2), has an overdamped, non-oscillating flow velocity solution of the form shown by equation (18):

$$V(t) = V_2 \cosh\left(\omega_n \sqrt{\xi^2 - 1}\, t\right) e^{-\xi \omega_n t} \tag{18}$$

An overdamped FVW does not possess an oscillating component, as represented by equation (16), but an exponentially decaying component, with time constant "r" for the time constant of the exponential decay of the FVW, is as given by equation (19):

$$\tau = \frac{1}{\xi \omega_n} \tag{19}$$

Equation (19) indicates that, while the FWV may posses a non-oscillating exponentially decaying characteristic, the FWV is described, as for the underdamped FVW, by a damping coefficient and a natural resonant frequency.

For overdamped waveforms, for which there is no overshoot, to determine values for DC and DRF, more than two measurement points are normally required, with values for DC and DRF obtained through curve fitting of equation (18) to the measured FVW using established curve fitting algorithms and software operators.

In healthy macrocirculation arteries of diameter greater than 6 millimeters, with well matched impedances for arterial junctions and bifurcations, backward wave reflection may be negligible, in which case only two measurement points on the FVW are needed to determine values for the parameters $\omega_n$ and $\xi$.

Healthy central macrocirculation arteries are normally sufficiently elastic that their FWVs display oscillatory underdamped response characteristics, like those represented in FIG. 2, wherein such arteries have a damping coefficient which is less than unity. Central macrocirculation arteries (diameter greater than 6 mm) which do not present an underdamped oscillating FVW, but present a non-oscillating (monophasic) FVW, are taken to possess abnormal morphology or elasticity characteristics which, from a medical diagnosis perspective, may predict arteriosclerotic and/or atherosclerotic development.

Healthy arteries in the mesocirculation, arteries in which the artery's resistive impedance to pulsatile flow increases with decreasing diameter, the damping coefficient increases from less than unity (underdamped) to greater than unity (overdamped). Hence, mesocirculation arteries of diameter less than the critical diameter of about 4 mm may present a non-oscillating FVW characteristic.

Referring to equation (14), using alternate symbology, the flow velocity "V(t)" of the underdamped FVW of equation (14) may be rewritten as equation (20) for time after $T_2$ the time of occurrence of the peak forward systolic flow velocity:

$$V(t) = V_2 \cos(DRF * (t - T_2)) e^{-DC*NRF(t-T_2)} \tag{20}$$

Where a, =NRF, the Natural Resonant Frequency, $\omega_d$=DRF, the Damped Resonant Frequency, $\xi$=DC, the Damping Coefficient, and $T_2$ is the time at which the systolic flow velocity maximum occurs, wherein such time is relative to the foot of the FVW, the instant in time immediately preceding the rapid rise of the systolic pulse.

While the representative FVW shown in FIG. 2 was measured non-invasively using the pulse wave Doppler mode of a medical ultrasound scanning device, similar FVWs may be obtained non-invasively using other blood flow velocimetry devices including, but not limited to, Phase Contrast Magnetic Resonant Imaging and X-Ray Digital Subtraction systems. The method of this disclosure is applicable to FVW-based, NRF measurements, irrespective of the velocimetry device employed to measure the FVW.

FVWs can also be invasively measured using intravascular sensors, often implemented in fiber optics and/or solid-state laser devices, which can measure cellular flow rate, pulse flow velocity or Doppler shift (with lasers, at the frequency of light waves).

Intravenous injection of various dyes or nanoparticles into the blood stream can also be employed to enhance the magnetic, radiation or reflective properties of moving blood cells and have been employed in the measurement of blood flow velocity, particularly in narrow arteries, both invasively and non-invasively.

It is an objective of this disclosure to provide an apparatus and method for the measurement of indices of arterial elasticity and stiffness based on the detection and measurement of specific values of flow velocity on an underdamped oscillating FVW, resulting in the determination of values for damped resonant frequency (DRF), damping coefficient (DC), and natural resonant frequency (NRF), parameters which describe the FVW, irrespective of the physics phenomena on which the damped oscillatory FVW measurement is based.

The method and apparatus for the measurement of Natural Resonant Frequency (NRF) of a FVW, as described in this disclosure, overcomes many of the clinical use limitations inherent in the measurement of the Pulse Wave Velocity (PWV) of a propagating pressure pulse using a dual pressure sensor approach.

The device which is the most widely deployed and most clinically used as a pulsatile blood flow velocity detecting unit is the pulse Doppler ultrasound scanning device. For the provision of a detailed description of a specific apparatus for obtaining indices of arterial elasticity and stiffness, based on blood flow velocity measurements, the specific apparatus focus of this disclosure is that of a pulse Doppler ultrasound scanning device, but the method is more generally applicable to any flow velocity measurement device which produces a damped FVW Doppler ultrasonography is widely used in clinical settings and by primary care providers. Doppler ultrasound systems are relatively inexpensive, and measurements can be made in the limited time normally available for testing in a clinical setting. Doppler ultrasound systems offer the ability to measure pulsatile blood flow velocities at depths of 30 centimeters, or more, below the skin's surface, dependent on the frequency of the ultrasound signal. A representative flow velocity waveform, as captured in-vivo using Doppler ultrasound on a healthy, resting macrocirculation artery, is as shown in FIG. 2. The representative measured FVW shown in FIG. 2 is categorized in the medical community as "multi-phasic", wherein the flow velocity oscillates one or more times around the steady state flow velocity which is at the centre of the FWV's exponential decay envelope.

Currently available medical pulse Doppler ultrasound scanning systems employ digital signal processing and digital computing in the processing and analysis of the analog ultrasound echo signals received by the detection sensor of the system. Medical pulse Doppler ultrasound scanning systems are currently available which employ commercial computers, computing tablets and/or smartphones, wherein the Doppler flow velocity detector transmits, by Wi-Fi, Bluetooth or other wireless communication protocol, detected ultrasound echo signals to commercial computing devices, wherein the commercial computing devices execute the various processing and computing steps required to convert the ultrasound echo signal into images and parameters that may be used by medical personal for analysis and diagnosis purposes.

The current disclosure provides an apparatus and method which may be implemented in currently available Doppler ultrasound systems, through the modification and/or addition of software algorithms and operators to such currently available ultrasound systems, (including associated computing devices), the measurement of indices of arterial elasticity and stiffness, measurements of importance in the medical diagnosis of cardiovascular diseases and all-cause mortality.

The current disclosure provides an apparatus and method for the measurement of several different indices of arterial stiffness, including Pulse Wave Velocity (PWV), a long-established index of arterial stiffness, and Natural Resonance Frequency (NRF), a novel index of arterial elasticity. Natural Resonant Frequency, measured at a location in an artery, is proportional to Pulse Wave Velocity (PWV) at the same location, with the constant of proportionality between NRF and PWV being the length of elastic artery, wherein the length is determined by the resistive impedance to pulsatile flow being negligible compared to the elastic/inertial reactive impedance.

The current disclosure provides an apparatus and method for determining NRF from a pulse flow velocity waveform (FVW), not a pulse pressure velocity waveform, as is used in PWV measurement, with flow velocity measured at a single arterial location, without requiring measurements at two separate arterial locations. As described hereafter, the NRF can be determined directly from measured flow velocity values at specific points on the FVW.

The current disclosure provides an apparatus and method for the measurement of a PWV Gradient, a proposed predictor of all-cause mortality, wherein the gradient of PWV may occur across arterial morphology irregularities and abnormalities, such as arterial stenoses, bifurcations, and sclerotic plaques.

The current disclosure provides an apparatus for the measurement of the difference between a clinically measured FVW and a computed FVW, wherein a computed FVW is that computed by applying clinically measured values of a FVW's systolic maximum flow velocity and maximum overshoot flow velocity (also referred to as local minimum flow velocity), and their timings, to equation (14) and to compute the difference in value, instant-by-instant, between the clinically measured and computed FVW. The root mean square difference or variance between the clinically measured FVW and the computed FVW is proposed as a novel new measure and index of abnormality in arterial morphology, wherein such abnormality causes the measured FVW to vary from a computed FVW solution to the linear second order damped flow velocity response as described an equation of the form of that of equation (2).

Figure 5:
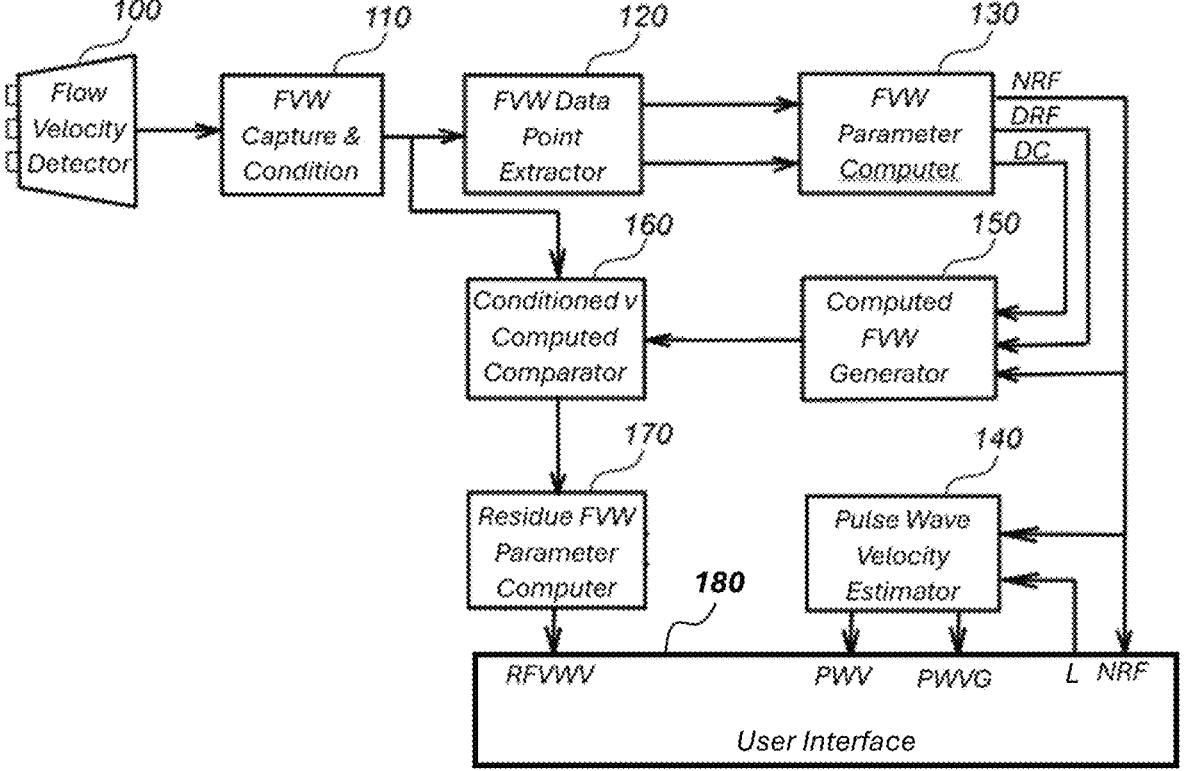
FIG. 5 is an overview schematic block diagram showing the structure and inter-relationships of the primary components of this disclosure.

The schematic block diagram of FIG. 5 outlines the structure and inter-relationships of the primary components of the apparatus and method disclosed here.

The flow diagram of FIG. 6 complements the outline structure and inter-relationships of the primary components as identified in the block diagram of FIG. 5, by identifying the basic functionality of each of the units of FIG. 5.

Referring to the schematic block diagram of FIG. 5, an embodiment of this disclosure provides for a Flow Velocity Detecting unit, unit 100, (also referred to as a Flow Velocity Detector), placed on the skin's surface over an artery, wherein such detector, if using Doppler ultrasound flow velocity measurements, emits a soundwave at a frequency, which, when reflected from moving blood, is shifted in frequency, wherein the frequency shift is a measure of the velocity of blood flow. With the velocity of blood flow varying across the arterial lumen, at any instant on the received flow velocity waveform (FVW), multiple velocities may be received simultaneously by the detector, as represented by the width (vertical extent) of the representative waveform shown in FIG. 2.

The measurement of specific flow velocity values, particularly at local maxima in forward and backward flow, as evidenced by the pulse Doppler ultrasound measured waveform of FIG. 2, at different time points on a single FVW, and the use of those measured values, as described herein, provides the means to determine a new index of arterial elasticity, as described by Natural Resonant Frequency (NRF), at a specific arterial location.

Referring to FIG. 5, unit 100, the Flow Velocity Detecting unit detects the velocity of the blood's flow in the artery under measurement, instant-by-instant, for a duration of time which may comprise one or more cardiac cycles. Unit 100 may be implemented, for example, by a pulse Doppler ultrasound scanner or other blood flow velocimeter, which detects pulse flow velocity, instant-by-instant, in a pulsatile wave, wherein such wave may possess a spread in the velocity spectrum at each instant in the wave. Unit 100, the Flow Velocity Detecting unit outputs the detected "unconditioned" flow velocities, wherein such unconditioned pulsatile flow wave potentially includes multiple simultaneous flow velocities, instant by instant, to unit 110, the flow velocity wave (FVW) Capture and Condition unit (also referred to here as the automatic capture and condition unit).

The detected flow velocities output from unit 100, the Flow Velocity Detector, into unit 110, the Capture and Condition unit, may be in analog or digital format. The output flow velocity measurements from unit 100 are described as "unconditioned" in that they may be multivalued at each instant in time and are unprocessed by any filtering, averaging or other process for converting the velocity measurements into a smoothly varying, single-valued plot, instant-by-instant, of flow velocity, suitable for subsequent computational processing.

The functions which each of the units shown in FIG. 5 perform on a FVW, subsequent to the detection of the FVW, are executed using established computational and/or digital signal processing devices or systems, using software languages or programs which possess established operators for the execution of the required mathematical operations, data storage, data retrieval and related functions.

This disclosure identifies the functions and computations needed to implement the disclosed invention but is silent on the selection of any specific software language or languages selected to implement such functions and computations. Existing medical Doppler ultrasound scanning devices currently perform functions and computations using various software languages like those needed to implement the apparatus and methodology of this disclosure. The functions, software languages and computation al operations required to implement the apparatus and methods of this disclosure are implementable by practitioners involved in the digital and software processing of medical Doppler ultrasound systems and measurements.

Referring to FIG. 5, unit 110, the FVW Capture and Condition unit, receives, instant-by-instant, "unconditioned" flow velocity values from unit 100. If such values are in analog format, unit 110 performs analog-to-digital conversion, instant-by-instant, using commercial sample-and-hold devices with such digitized values of flow velocity output from such sample-and-hold device being stored, instant-by-instant, in a digital memory device within unit 110. If, however, the detected flow velocity output values input from unit 100 are in digital format, they are stored directly, instant-by-instant, in digital memory in unit 110. A complete multivalued flow velocity waveform (FVW), as stored in digital memory in unit 110, is comprised of flow velocity values, instant-by-instant, for the duration of one cardiac cycle.

One embodiment of this disclosure provides for unit 110, the Capture and Condition unit, to synchronize multiple sequential cardiac cycles of flow velocity, using the foot of the FVW, or an electrocardiographic pulse for synchronization, cardiac cycle to cardiac cycle, to sum using established software operations, instant-by-instant, flow velocities from multiple synchronized and overlaid FVWs, and to store in digital memory, in near real time, a multivalued FVW which may be comprised of multiple detected cardiac cycles, overlaid on one another.

One embodiment of unit 110 (FIG. 5), the FVW Capture and Condition unit, provides for the application of near real-time anti-aliasing signal processing, to remove secondary pulse Doppler returns, wherein such anti-aliasing signal processing algorithms and operators are established, not only for use in medical Doppler scanning devices, but also in pulse Doppler radar systems.

Another embodiment of the unit 110, FVW Capture and Condition unit, provides for the use of real time anti-speckle signal processing to filter non-coherent scattering of ultrasound pulse returns from individual scattering sites, wherein such anti-speckle signal processing is established, not only in medical Doppler scanning devices but also in pulse Doppler radar systems.

Anti-alias, anti-speckle and related digital signal processing techniques applied to an unconditioned FVW require near real time signal processing to enable subsequent processing to be carried out in near real time, in order that arterial elasticity measurements can be executed quickly for use in clinical settings.

Unit 110 (FIG. 5), the FVW Capture and Condition unit, reduces a stored multivalued FVW, instant-by-instant, to a single valued FVW, which is also stored, using established software operations, in digital memory, by processing the multi-valued FVW using digital filtering, digital peak detection and/or digital averaging and/or weighting signal processing, using existing software operators, thereby producing a single-valued FVW, instant-by-instant, which is directly related to its associated unconditioned FVW.

One embodiment of unit 110, the Capture and Condition unit, includes forward/backward averaging between adjacent flow velocity values on a single-valued FVW, using existing software operators, to generate a single-valued FVW which varies smoothly with time, thereby enabling the identification of the values and times of the peak systolic flow velocity and of the peak overshoot flow velocity. Such a smoothly varying, single-valued FVW is described here as a "conditioned" FVW.

Figure 7:
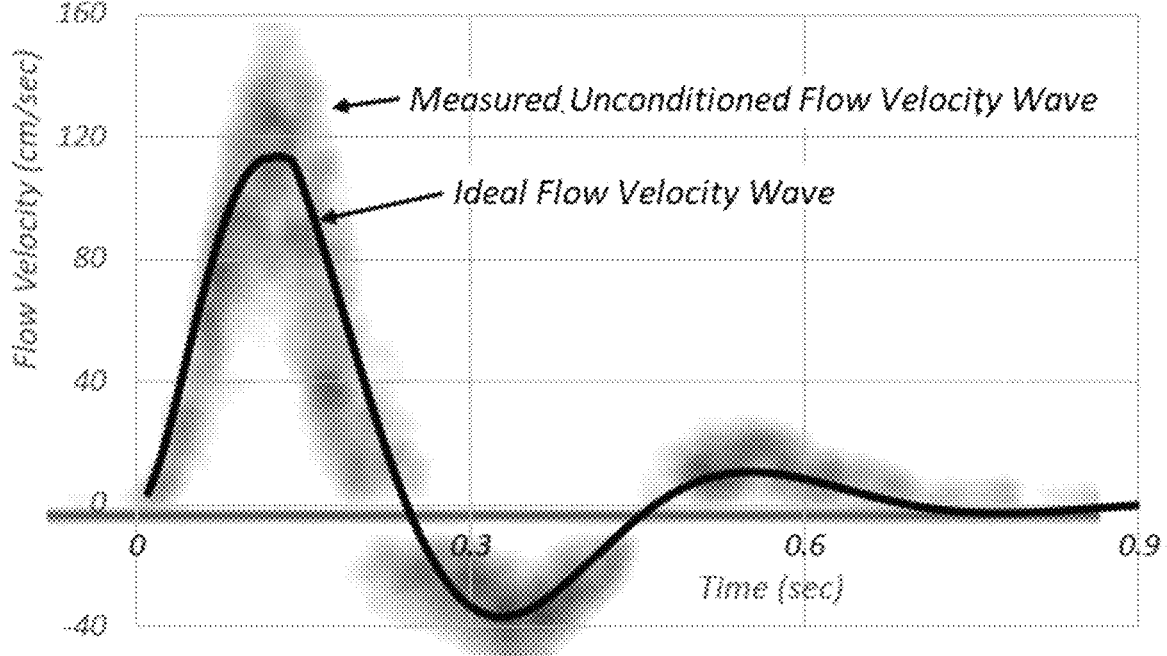
FIG. 7 is a representative underdamped FVW, determined in accordance with this disclosure, superimposed on the in-vivo Doppler ultrasound measured lower limb macrocirculation FVW of FIG. 2.

A "conditioned" FVW, as represented by the solid black line in FIG. 7, is superimposed on its associated "unconditioned" FVW, as shown in FIG. 7 (and which was also shown in FIG. 2). The conditioned FVW in FIG. 7 was calculated using equation (14). The match between the conditioned, calculated waveform and the unconditioned waveform, as shown in FIG. 7, provides evidence of the validity of equation (14) as a descriptor of the FVW The data points used to calculate the conditioned FVW, shown in FIG. 7, are based on the average of the spread in velocities, instant-by-instant, evident in the unconditioned FVW in FIGS. 2 and 7. Alternately the conditioned FVW may also be based on peak, mean, or other criteria for generating a single-valued, smoothed (conditioned) FVW which is directly related, instant-by-instant, to the unconditioned FVW.

Unit 110 (FIG. 5), the FVW Capture and Condition unit, outputs to unit 120, the Data Point Extraction unit (also referred to as Data Point Extractor), and to unit 160, the Condition vs Computed FVW Comparator unit, a conditioned, single valued, smoothed FVW, instant-by-instant, automatically and with granularity sufficient to meet the Nyquist minimum sampling rate criteria of at least two times the rate of the tenth harmonic of the heart beat. Such fine granularity implies preferred computational time steps that are less than, one-twentieth of the reciprocal of the heart rate.

Referring to FIG. 5, unit 120, the FVW Data Point Extraction unit, detects, measures and stores in digital memory, the maximum forward flow velocity of the conditioned FVW (from unit 110) at systole ($V_2$ in FIG. 4), and the instant in time on the FVW at which the systole maximum occurs ($T_2$ in FIG. 4), wherein such detection, measurement and storage in digital memory is executed using established software language and operators, operating in near real time.

Unit 120 (FIG. 5), the FVW Data Point Extraction unit, also detects, measures and stores in digital memory the local maximum overshoot flow velocity ($V_3$ in FIG. 4), (also referred to as local minimum velocity of flow) and the instant in time on the FVW of the maximum overshoot (local minimum) of flow velocity ($T_3$ in FIG. 4), wherein such detection, measurement and storage in digital memory is executed using established software language and operators. The maximum overshoot of flow velocity also corresponds to the local maximum flow velocity in the reverse flow direction (also referred to as local minimum velocity of flow), which immediately follows the systolic maximum flow velocity.

Unit 120 (FIG. 5), the FVW Data Point Extraction unit (also referred to as Data Point Extractor), receives a conditioned FVW from unit 110, the Capture and Condition unit, and extracts, wherein such extraction is executed using established software operators, and outputs to unit 130, the Flow Velocity Parameter Compute unit, (also referred to here as the FVW Parameter Computer) the following parameters:

a. the maximum flow velocity value ($V_2$ in FIG. 4), which occurs at systole, wherein such maximum flow velocity is relative to the steady state flow velocity ($V_0$, in FIG. 4).

b. the time of occurrence of the maximum flow velocity ($T_2$ in FIG. 4), wherein such time is relative to the foot of the FVW, c. the local maximum flow overshoot velocity value (which follows the maximum systolic flow velocity, $V_3$ in FIG. 4), wherein such maximum overshoot flow velocity is relative to the steady state flow velocity and, d. the time of occurrence of the local maximum flow overshoot ($T_3$ in FIG. 4), wherein such time is relative to the foot of the FVW One embodiment of unit 120 (FIG. 5), the FVW Data Point Extraction unit captures and stores in computer memory, in near real time, the specific flow velocities and time instances on the conditioned FVW which correspond to the maximum systolic velocity and the local overshoot maximum velocity (immediately following systole), wherein such velocity extractions are executed using established software operators in near real time.

Unit 120 (FIG. 5), the Data Point Extraction unit, detects, measures and stores in digital memory, using existing software operators, in near real time, values of $V_2$ and $V_3$, relative to the value of the steady state value for flow velocity $V_0$, which, in healthy central macrocirculation arteries, is approximately the flow velocity at end diastole.

For FVW measurements of mesocirculation arteries (with diameters greater than 1 mm but less than 6 mm), the end diastole flow velocity is not normally near zero. For such FVW measurements, detection and measurement of the two velocities, one at the FVW systole maximum and the other at the FVW overshoot maximum, relative to the steady state velocity, may not be sufficient to accurately compute the damping coefficient for the artery, but the damped resonant frequency can be determined from the timing of these two maxima. For such mesocirculation measurements, the damped resonant frequency can be used as an estimate of arterial elasticity, whereby the damped resonant frequency includes the effect of the non-negligible resistance to flow associated with the mesocirculation, and whereas the natural resonant frequency does not include the effect of non-negligible resistance to flow of arteries of diameter less than about 6 mm.

Unit 120 (FIG. 5), the Data Point Extraction unit, outputs the values of $V_2$, $V_3$, $T_2$ and $T_3$, to unit 130, the FVW Parameter Computer using established software operators, in near real time.

Referring to FIG. 5, unit 130, the FVW Parameter Computer, computes the value of the damped resonant frequency "$\omega_d$ or DRF" using equation (19), the value of damping coefficient "$\xi_d$ or DC" using equation (20), and the value of natural resonant frequency "$\omega_n$ or NRF" of the FVW, using equation (21), wherein each of these computations is executed using established software operators, in near real time.

Unit 130, the FVW Parameter Computer, computes the value of the damped resonant frequency "$\omega_d$ or DRF", in near real time using established software operators, by executing equation (21):

$$\omega_d = DRF = \frac{\pi}{T_3 - T_2}, \tag{21}$$

In equation (21) the time interval between the systolic maximum velocity and the local overshoot maximum immediately following systole ($T_3 - T_2$), represents one-half of a wavelength, or $\pi$ radians, of the DRE Unit 130, the FVW Parameter Computer, computes the value of the damping coefficient "or DC", in near real time using established software operators, by executing equation (22):

$$\xi_d = DC = \frac{1}{\pi} \ln \left| \frac{V_2}{V_3} \right|, \tag{22}$$

Wherein the flow velocity of the underdamped FVW, in one-half of a DRF wavelength, or in $\pi$ radians, is decreased proportional to the natural logarithm of the absolute value of the $V_2$ to $V_3$ ratio.

Unit 130, the FVW Parameter Computer, computes the value of the natural resonant frequency "$\omega_n$ or NRF", in near real time using established software operators, by executing equation (23), $$\omega_n = \frac{\omega_d}{\sqrt{1-\xi^2}} = NRF = DRF(1 - DC^2)^{-1/2} \tag{23}$$

Unit 130, the FVW Parameter Computer, computes values for DC, DRF and NRF, using established software operators, in near real time, to implement equations (19), (20) and (21), by applying input values of $T_2$, $T_3$, $V_2$ and $V_3$, to these equations.

Unit 130, the FVW Parameter Computer, outputs the value of NRF to unit 140, the PWV Estimation unit 140, and the values of DC, DRF and NRF to unit 150, the Computed FVW Generator (also referred to here as the flow waveform generator).

This disclosure provides for the measurement of values for DC, DRF and NRF through the measurement of flow velocities (relative to the steady state velocity) at maximum systolic and maximum overshoot flow velocities, and the timings of these velocity maxima on the FVW, (relative to the time of the start or foot of the FVW). This disclosure also provides for the measurement of flow velocities, with timings not specific to the systolic and overshoot maxima on a measured FVW, and computing values for DC, DRF and NRF; using established curve fitting algorithms and software operators, to match either equation (14) or (18), (depending on the existence of otherwise of damped oscillation in the artery's FVW response to an impulse of flow into the artery), to the measured data, thereby calculating values of DC, DRF and NRF which best curve fit the measured FVW data.

The value of natural resonant frequency (NRF) which is output from unit 130, the FVW Parameter Computer, represents a new diagnostic index of arterial elasticity. A database of measured values of arterial NRF; and the associated cardiovascular disease conditions, against which clinically measured values of NRF may be compared, potentially offers a new means for indexing arterial elasticity as a biomarker of cardiovascular disease and predictors of all-cause mortality. An arterial NRF; measured by pulse Doppler ultrasound, potentially offers a substantial methodology improvement for the measurement of indices of arterial elasticity, within the limited time available in clinical settings, compared to the current dual pulse pressure PWV measurement methodologies.

Referring to FIG. 5, unit 140, the PWV Estimation unit, receives values of NRF from unit 130 and also receives an estimate of the total length L of elastic macrocirculation artery, potentially entered manually, based on physiological measurements, (or a default value entered for the length L, which typically is in the range of L≈50 cm), wherein such measured length is estimated from the origin of the artery under measurement to the arterial location at which the arterial diameter is reduced to 6 mm. For example, for the central arteries such length would be from the aortic arch to the femoral artery in normal, healthy, non-sclerotic arteries, a value typically in the 50 cm range. L is a length wherein the damping coefficient is less than 0.4.

In cases of stenoses or sclerotic plaques that reduce a macrocirculation artery's diameter to approximately 6 mm, or less, at stenotic, morphologically abnormal locations, the estimated value of elastic artery length input into Unit 140 may be also reduced to the location of the abnormality, and may require physiological measurement of arterial length to the location of such morphological abnormality.

Unit 140, the PWV Estimation unit, estimates a value of PWV by computing equation (22) in near real time using established software operators, (see also equation (10)), by inputting an estimated value of L, and inputting the value of NRF from unit 130, the FVW Parameter Computer, into equation (24):

$$PWV = L^* NRF \tag{24}$$

The value of pulse wave velocity (PWV) is output by unit 140, the PWV Estimation unit, into unit 180, the User Interface, for the use of the medical personnel as a biomarker of cardiovascular disease and a predictor of all-cause mortality.

Unit 140, the PWV Estimation unit, may also output a value of PWV Gradient, into unit 189, the User Interface, wherein the gradient of NRF is calculated, using established software operators, as the ratio of two distinct NRF measurements, with one NRF measurement taken on one side of an arterial morphology change, such as an arterial bifurcation, stenosis or sclerotic plaque, and the second measurement taken on the other side of the arterial morphology change. The value of the gradient of PWV and the value of gradient of NRF are numerically equal as a consequence of equation (24), where L is common to both measurements.

The value of PWV Gradient is also output by unit 140, the PWV Estimation unit, into unit 180, the User Interface, for the use of the medical personnel in medical diagnosis as a predictor of all-cause mortality.

Referring to FIG. 5, unit 150, the Computed FVW Generator, receives values for NRF, DRF and DC from unit 130, the FVW Parameter Computer, and computes equation (18) to generate values of flow velocity, instant-by-instant, for one cardiac cycle (the length of one FVW), using established software operators. Unit 150 generates a Computed FVW, as represented by the graphic in FIG. 7. Unit 150 generates a Computed FVW in near real time and with granularity sufficient to significantly exceed the Nyquist sampling rate of at least two times the rate of the tenth harmonic of the heartbeat. Such fine granularity implies preferred computational time steps that are no larger than the one-twentieth of the reciprocal of the heart rate.

Figure 8:
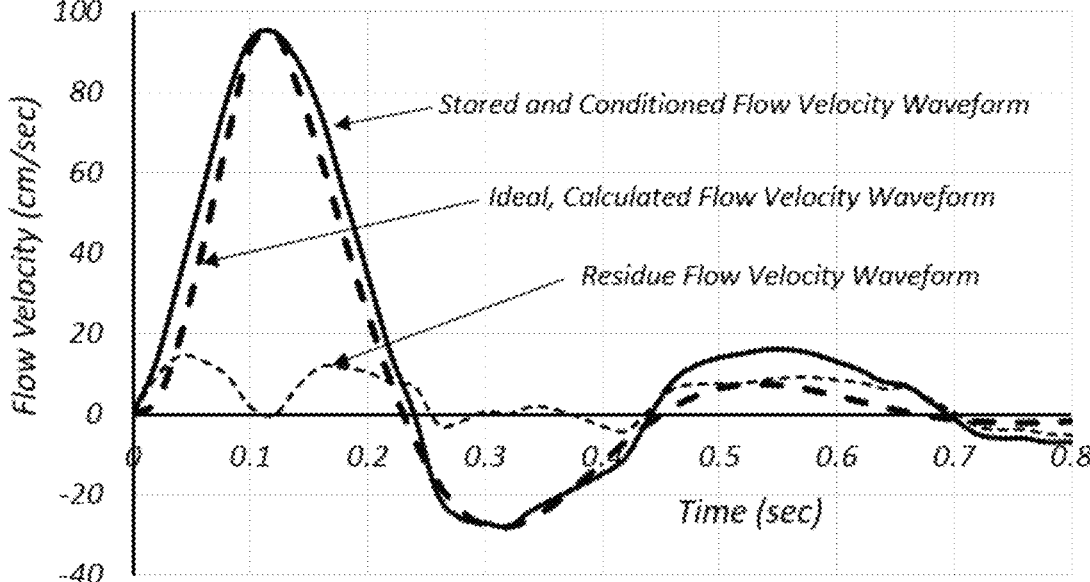
FIG. 8 shows several underdamped flow velocity waveforms, one of which, a computed FVW, as determined in accordance with this disclosure, by applying the in-vivo Doppler ultrasound measured velocities and their times, with such computed FVW overlaid on a reported femoral artery Doppler ultrasound in-vivo measured and averaged FVW. The residue FVW for the variance between the disclosure's computed FVW and the measured FVW is also shown in FIG. 8.

Confirmation that the method and apparatus of this disclosure computes a FVW which matches that clinically measured, for a healthy macrocirculation artery, using pulse Doppler ultrasound, is provided in FIG. 8. In FIG. 8, a calculated FVW (dashed line), as determined using the apparatus and method of this disclosure, is overlaid on an in-vitro clinically measured FVW (solid line). The values for DC, DRF and NRF which were input into FVW equation (20), to generate the computed FVW, were extracted from the in-vivo measured waveform of FIG. 8 and are included in the Table below of measured and computed FVW parameters.

| Overlay | Peak | Peak | Ideal | Peak | Peak | Damped | Natural | Compliant | Pulse |
|---|---|---|---|---|---|---|---|---|---|
| Femoral PFVWs Ideal vs Measured | Reverse Velocity | Forward Velocity | Damping Coefficient | Reverse Time | Forward Time | Resonant Frequency | Resonant Frequency | Artery Length | Wave Velocity |
| Symbol | V₁ | V₂ | DC | T₃ | T₂ | DRF | NRF | l | PWV |
| Units | cm/s | cm/s | none | sec | sec | rad/s | rad/s | m | m/s |
| Measured or estimated | 26 | 96 | | 0.35 | 0.13 | | | | 7.90 |
| Calculated | | | 0.42 | | | 14.28 | 15.70 | 0.5 | 7.85 |

The close match, evidenced in FIG. 8, between the in-vivo measured FVW and the calculated FVW, wherein the calculated FVW was generated using the method and apparatus of this disclosure, provides evidence of the validity of the method and apparatus of this disclosure.

The value of NRF, the new measure of arterial elasticity, calculated using the method and apparatus of this disclosure, (particularly equations 23, 24 and 25) and as shown in the table, is NRF=15.70 radians/sec.

A value for the pulse wave velocity (PWV) can be estimated with the application of equation (24), by multiplying the estimated length of elastic artery (L≈50 cm) by the calculated value of NRF=15.7 rad/sec, producing an estimated value PWV=7.85 m/sec.

The value of PWV=7.85 m/sec, as calculated using the apparatus and method of this disclosure, (equation 24) is a good match to the clinically measured arterial stiffness value of PWV=7.90 m/sec as measured using the dual-pressure pulse PWV measurement technique.

The close match between the values of PWV, calculated using the apparatus and method of this disclosure, and that measured using the dual-pulse pressure measurement technique, provides further validation of the apparatus and method of the disclosure.

The value of PWV, obtained by applying the method and apparatus of this disclosure, is not only a significant biomarker of cardiovascular disease and predictor of all-cause mortality, but is also obtainable, using a pulse Doppler ultrasound measurement technique that is suitable for rapid diagnosis in a clinical setting, representing a substantial improvement over the currently used dual pressure sensor PWV measurement techniques for clinical use.

The computed FVW generated by unit 150, the Computed FVW Generator is input, instant-by-instant, into unit 160, the Conditioned vs Computed FVW Comparator (also referred to as flow wave comparison unit). The conditioned FVW generated by unit 120, the Capture and Condition unit, is also input, instant-by instant, into the FVW Comparator unit 160. Unit 160, compares and computes, using established software operators, instant-by-instant, the difference in value between the conditioned and the computed FVWs.

Referring to FIG. 5, unit 160, the Conditioned vs Computed FVW Comparator unit, generates a difference or residue FVW, using established software operators, which is the difference in flow velocity, instant-by-instant, between the conditioned FVW input from unit 120 and the computed FVW input from unit 150. A representative Residue FVW, the instant-by-instant difference between the conditioned and the computed FVWs, is shown by the dotted line in FIG. 8. Unit 160 outputs the difference, or residue FVW, instant-by-instant, into unit 170, the Residue FVW Parameter Computer (also referred to as the residue flow waveform parameter data extract and computer unit).

Referring to FIG. 5, unit 170, the Residue FVW Parameter Computer, receives the residue FVW, instant-by-instant, from unit 160, the Conditioned vs Computed FVW Comparator unit and computes the root mean square (RMS)

value or variance of the Residue FVW, using established software operators, and unit 170 outputs the Residue FVW Variance (RFVWV) value into unit 180, the User Interface unit, as a novel index of arterial morphology abnormality, in near real time, for clinical use and immediate medical diagnosis purposes.

The variance of the Conditioned FVW from that of the Computed FVW, wherein such variance may be associated with arterial morphology abnormalities, is a potentially useful index for use in medical diagnosis. A value of RFVWV, when related to a database of parametric values of Residue FVW Variance, as a function of cardiovascular disease, yet to be established, would provide a new means for cardiovascular disease analysis and diagnosis.

The current disclosure provides an apparatus and method for implementation in currently available Doppler ultrasound systems, through modification and/or addition of software algorithms and operators to currently available commercial medical ultrasound scanning devices. Commercial Doppler ultrasound scanners are currently widely deployed in doctor's offices and clinics around the world. Many of these scanners could be adapted easily using the apparatus and method of this disclosure, providing the ability for doctors, imaging clinics and point-of-care practitioners, around to carry out arterial elasticity and stiffness measurements for cardiovascular disease diagnosis and mortality prediction.

Figure 9:
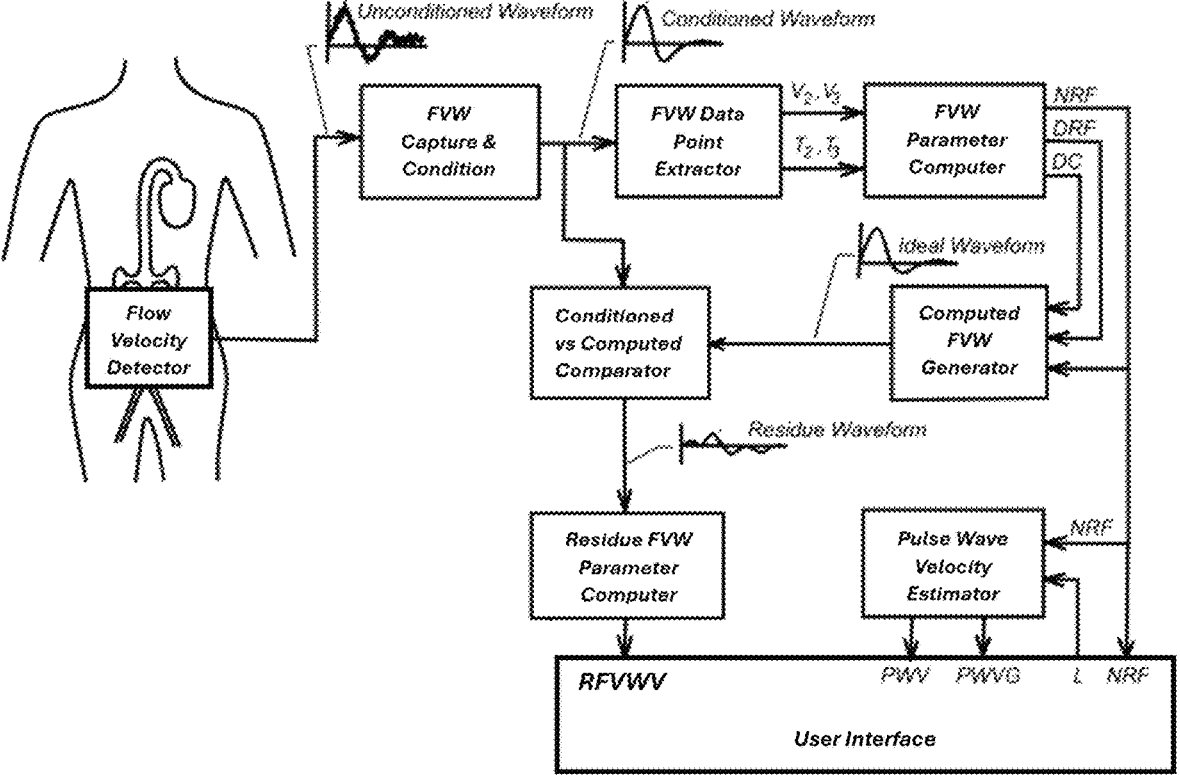
FIG. 9 is a schematic block diagram showing representations of the unconditioned, the conditioned, the computed and the residue FVWs in relation to the primary components of the disclosure.

In summary, and referring to FIG. 9, the flow velocity waveforms at various points in the apparatus, are represented. The velocity of blood flow in an artery is detected by the Flow Velocity Detector, unit 100, by placing the detector over an artery. The arteries of greatest medical relevance include the common carotid, the coronary, the thoracic aorta, the renal arteries, the abdominal aorta, the iliac and femoral arteries. The detected and unconditioned flow velocity wave at any instant in the waveform contains multiple simultaneous velocities associated with the spread of velocities across the lumen of the artery. The unconditioned FVW depicted in FIG. 9, may also contain artifacts from such sources as respiratory noise, noise from turbulent flow, speckle noise from non-coherent scatterers, secondary alias ultrasonic echo returns and antegrade flow FWVs which are reflected from arterial morphology disruptions such as those posed by bifurcations, stenoses and sclerotic plaques.

Before the extraction of key velocity and time data from the detected flow velocity signal, a single valued smooth waveform is required. Unit 110, the FVW Capture and Condition unit, captures, stores and overlays a plurality of cardiac cycles of detected flow velocity waveforms. Unit 110 outputs a conditioned FVW, as shown in FIG. 9 which is a smoothly varying, single valued waveform, in which the detected flow velocity has been smoothed to produce a conditioned FVW The conditioned FVW is output from unit 110 into unit 160, the Conditioned vs Computed FVW Comparator.

The conditioned FVW is also output from unit 110 into unit 120, the FVW Data Point Extractor. The Data Point Extractor extracts and outputs to Unit 130, the maximum systolic flow velocity, $V_2$, which occurs at time, $T_2$. Unit 120 also extracts the maximum overshoot flow velocity $V_3$, which occurs at time, $T_3$. Unit 130 applies the input values of $V_2$, $T_2$, $V_3$ and $T_3$ to compute values for damping coefficient (DC), damped resonant frequency (DRF), and natural resonant frequency (NRF), of a flow velocity waveform as depicted in FIG. 9, which is an estimate of the conditioned FVW, as shown in FIG. 9, with specific matches at the local maximum systolic and overshoot flow velocities.

The relationships between unit 140 input parameters $V_2$, $T_2$, $V_3$ and $T_3$ and output parameter, DC, DRF and NRF, are as follows:

$$DC = \frac{1}{\pi}\ln\left|\frac{V_2}{V_3}\right|, \; DRF = \frac{\pi}{T_3 - T_2}, \; \text{and} \; NRF = DRF\left(1 - DC^2\right)^{-1/2} \quad (25)$$

NRF is output into unit 180, the User Interface, as a new index of arterial elasticity, a biomarker of cardiovascular disease and predictor of all-cause mortality.

The natural resonant frequency (NRF) output from unit 130, the FWV Parameter Computer is also input into unit 140 the PWV Estimator. The relationship between the NRF input into unit 150 and the pulse wave velocity (PWV) estimation calculated by unit 140 is as follows:

PWV=L*NRF where the length L is the length of primarily elastic artery which, for the aorta, extends from the aortic arch to the location at which the artery diameter has diminished to 6 millimeters, a length in the range of 50 cm. L is input into unit 140 from unit 180, the User Interface.

PWV is an established index of arterial stiffness, a biomarker of cardiovascular disease and predictor of all-cause mortality and is output into unit 180, the User Interface.

The output of unit 140 the Computed FVW Generator, that of a computed FWV, is input into unit 160, the Conditioned vs Computed FWV Comparison unit. Unit 160 calculates the difference in flow velocities, point by point, between the conditioned and computed FVWs and unit 160 outputs the difference as the residue FVW (as shown in FIG. 9), into unit 170, the residue FVW parameter calculator.

Unit 170 computes and outputs the output into unit 180, the variance between the computed and conditioned FVWs, which is the root mean square difference between the computed and conditioned FVWs, a measure of the deviation of a clinically measured elastic response of an elastic artery from that of the elastic response solution to the second order differential equation of the form of equation (2).

FVW Variance is proposed as a new index of arterial elastic condition.

The invention claimed is:

1. An ultrasonic Doppler apparatus for measuring elasticity and stiffness of an artery at a single measurement location about an artery, comprising:

a flow velocity detecting unit for emitting sound waves about the location and adapted to detect a plurality of blood flow velocities at the location of the artery in response to emitted soundwaves;

an automatic capture and condition unit having digital memory coupled to receive flow velocity data from the plurality of blood flow velocities, said automatic capture and condition unit adapted to extract, store in the digital memory, and condition a flow velocity waveform utilizing the stored flow velocity data so as to provide a conditioned flow velocity waveform related to the detected plurality blood flow velocities, wherein the conditioned flow velocity waveform is a waveform having a single-value, at each instant in time on the waveform, smoothly varying, instant to instant;

a data point extraction unit adapted to receive the conditioned flow velocity waveform and automatically capture from the conditioned waveform a local maximum velocity of pulse flow velocity $V_2$ at a time $T_2$, and a-local minimum velocity of flow velocity $V_3$ at a time $T_3$; and, a flow velocity parameter compute unit adapted to receive information processed by the data point extraction unit for automatically calculating a damped resonant frequency (DRF), a damping coefficient (DC) and a natural resonant frequency (NRF), related to the flow velocity waveform, in dependence upon a difference in the time between $T_3$ and $T_2$ and an absolute value of the ratio of $V_3$ to $V_2$, wherein the NRF is a measure of artery elasticity at the location in the artery, wherein NRF is related to pulse wave velocity (PWV) at the location, and wherein pulse wave velocity is an index of arterial stiffness at the location of the artery.

2. The ultrasonic Doppler apparatus for measuring elasticity and stiffness as defined in claim 1, wherein the damped resonant frequency is calculated by:

$$DRF = \frac{\pi}{T_3 - T_2}.$$

3. The ultrasonic Doppler apparatus for measuring elasticity and stiffness as defined in claim 2 wherein the damping coefficient is calculated by:

$$DC = \frac{1}{\pi}\ln\left|\frac{V_2}{V_3}\right|.$$

4. The ultrasonic Doppler apparatus for measuring elasticity and stiffness as defined in claim 3 wherein the NRF is calculated by:

$$NRF = DRF * \left(1 - DC^2\right)^{-1/2}.$$

5. The ultrasonic Doppler apparatus for measuring elasticity and stiffness as defined in claim 1 wherein PWV is calculated by:

PWV=L*NRF, PWV=L*NRF, where L as a length between two points along the artery where the artery diameter is greater than 6 millimeters along the portion between the two points.

6. The ultrasonic Doppler apparatus for measuring elasticity and stiffness as defined in claim 4, including a flow waveform generator unit for generating a damped oscillation flow velocity waveform related to the damping coefficient, the damped resonant frequency and the natural resonant frequency.

7. The ultrasonic Doppler apparatus for measuring elasticity and stiffness as defined in claim 6, including a flow velocity wave comparison unit for comparing the conditioned flow velocity waveform to a computed damped oscillation flow velocity waveform providing a residue flow velocity waveform.

8. The ultrasonic Doppler apparatus for measuring elasticity and stiffness as defined in claim 7, including a residue flow velocity waveform parameter data extract and compute unit for providing the root mean square (RMS) variance between a computed damped oscillating flow velocity waveform and the conditioned flow velocity waveform.

9. The ultrasonic Doppler apparatus for measuring elasticity and stiffness as defined in claim 4 wherein the flow velocity detector unit is one of a Doppler ultrasound device, an MRI device and, X-ray digital subtraction device.

* * * * *